`United States Patent` [19]

Takamizawa

[11] 4,019,169
[45] Apr. 19, 1977

[54] ULTRASONIC WAVE TRANSMITTING AND RECEIVING APPARATUS

[75] Inventor: Kinya Takamizawa, Yokohama, Japan

[73] Assignee: Tokyo Shibaura Electric Co., Ltd., Kawasaki, Japan

[22] Filed: Sept. 24, 1975

[21] Appl. No.: 616,390

[30] Foreign Application Priority Data

Sept. 30, 1974 Japan .............................. 49-111626

[52] U.S. Cl. ............................... 340/1 R; 73/67.8 S
[51] Int. Cl.² ............................................ G01S 9/66
[58] Field of Search ........................... 340/1 R, 3 A; 73/67.8 S

[56] References Cited

UNITED STATES PATENTS

| | | | |
|---|---|---|---|
| 3,919,683 | 11/1975 | Itamura et al. | 340/1 R |
| 3,936,791 | 2/1976 | Kossoff | 340/1 R |

*Primary Examiner*—Richard A. Farley
*Attorney, Agent, or Firm*—Oblon, Fisher, Spivak, McClelland & Maier

[57] ABSTRACT

An ultrasonic wave transmitting and receiving apparatus includes a control pulse generator for sequentially generating control pulses from its output terminals with a cyclically varied delay time. The control pulses are controlled in such a delay time relation as to enable the beams of ultrasonic waves to be deflected in left and right directions. The output pulse signals of deflection control units are controlled in such a delay time relation as to permit the beams of ultrasonic waves to be brought into focus by electron focussing control units. By the output pulses of the electron focussing control units, drive pulse generators are driven to supply drive pulses to electroacoustic conversion elements for generating the above-mentioned beams of ultrasonic waves. Some of the ultrasonic waves radiated in a medium is reflected at a boundary between two objects different in physical property (acoustic impedance) from each other and converted through the electroacoustic conversion elements to electric signals. The reflection wave signals so converted are sequentially stored in memory units, the contents of which are read out in response to the output pulse signals of the electronic focussing control units. The readout signals are, after being added together, supplied to a cathode ray tube.

10 Claims, 7 Drawing Figures

ULTRASONIC WAVE TRANSMITTING AND RECEIVING APPARATUS

This invention relates to an ultrasonic wave transmitting and receiving apparatus, and in particular an ultrasonic wave transmitting and receiving apparatus using an ultrasonic wave diagnosis.

An ultrasonic transmitting and receiving apparatus is adapted to display a two-dimensional real time image on a cathode ray tube by electronically phase-controlling the transmitting signals supplied to electro-acoustic conversion elements and received signals reflected from a subject through the electro-acoustic conversion elements. In the prior art the phase control is conducted using L.C. delay lines. For example, ULTRASONICS, vol. 6 pp153–159, July 1968, J. C. Somer discloses a high speed scanning system for ultrasonic medical diagnosis. In this apparatus, trigger pulses from an oscillator are supplied through first analog switches to delay lines each set to a predetermined delay time. Output pulses from the delay lines are supplied through second analog switches to pulse generators. The pulse generators, each, generate a high voltage impulse in response to a delay time on the corresponding delay line to drive the corresponding electro-acoustic conversion element permitting the beam of ultrasonic wave to be radiated from the electro-acoustic conversion element to medium. On the other hand, reflection waves enter, into the electro-acoustic conversion elements where they are converted to electric signals. The electric signals are supplied through the first analog switch to the delay lines so that they are controlled to have the same delay time. The received signals from the delay lines are added together, after passage through the second analog switches, amplified and supplied to a cathode ray tube.

The above-mentioned conventional ultrasonic diagnosis equipment using such L.C. lines has the disadvantages that it is very difficult to widen the band-width of the frequency, it is necessary to make the adjustments of the individual delay lines, and it is impossible to obtain the accurate delay time. Furthermore, a greater delay time results in an enlarged delay line. As a consequence, the apparatus per se is made bulkier with lowered stability against temperatures and humidity. The transmitting and receiving apparatus which is composed of the analog switches results in a very complicated circuit arrangement.

It is accordingly an object of this invention to provide an ultrasonic transmitting and receiving apparatus capable of effecting phase control of transmitting and receiving signals without using any delay lines.

Another object of this invention is to provide an ultrasonic wave transmitting and receiving apparatus capable of deflecting the beams of ultrasonic waves in the right and left directions of an array of electro-acoustic conversion elements.

Another object of this invention is to provide an ultrasonic wave transmitting and receiving apparatus capable of focussing the beams of ultrasonic waves into any points.

According to this invention, a pulse generator comprises a first counter circuit the preset values of which are sequentially varied by first clock pulses and a second counter circuit adapted to cause its preset values to be varied by the output of the first counter circuit and frequency-divide in accordance with the preset values second clock pulses having a higher frequency than that of the first clock pulses, and is designed to sequentially generate output pulses from its ouput terminals in response to the frequency-divided clock pulses of the second counter circuit and in a delay time relation corresponding to the frequency-divided clock pulses. Deflection control units are coupled to the control pulse generator and generate output signals in response to any one of the cyclically varied preset values of the second counter circuit i.e. the control output pulse generated in a predetermined delay time relation from the control pulse generator. Electronic focussing control units are coupled to the corresponding deflection control units and adapted to control the output signal of the deflection control units in such a predetermined delay time relation as to generate output pulses for focussing the ultrasonic beam. By the output pulses of the electronic focussing control units, drive pulse generators are driven to supply high voltage impulse to electro-acoustic conversion elements. In a reception, analogue memory units are adapted to store the received signals generated in the conversion elements and read out by electric signals with predetermined delay time. The readout signals are, after being added together, supplied to a cathode ray tube for two-dimensional display.

This invention can be more fully understood from the following detailed description when taken in conjunction with the accompanying drawings, in which.

Figure 1:
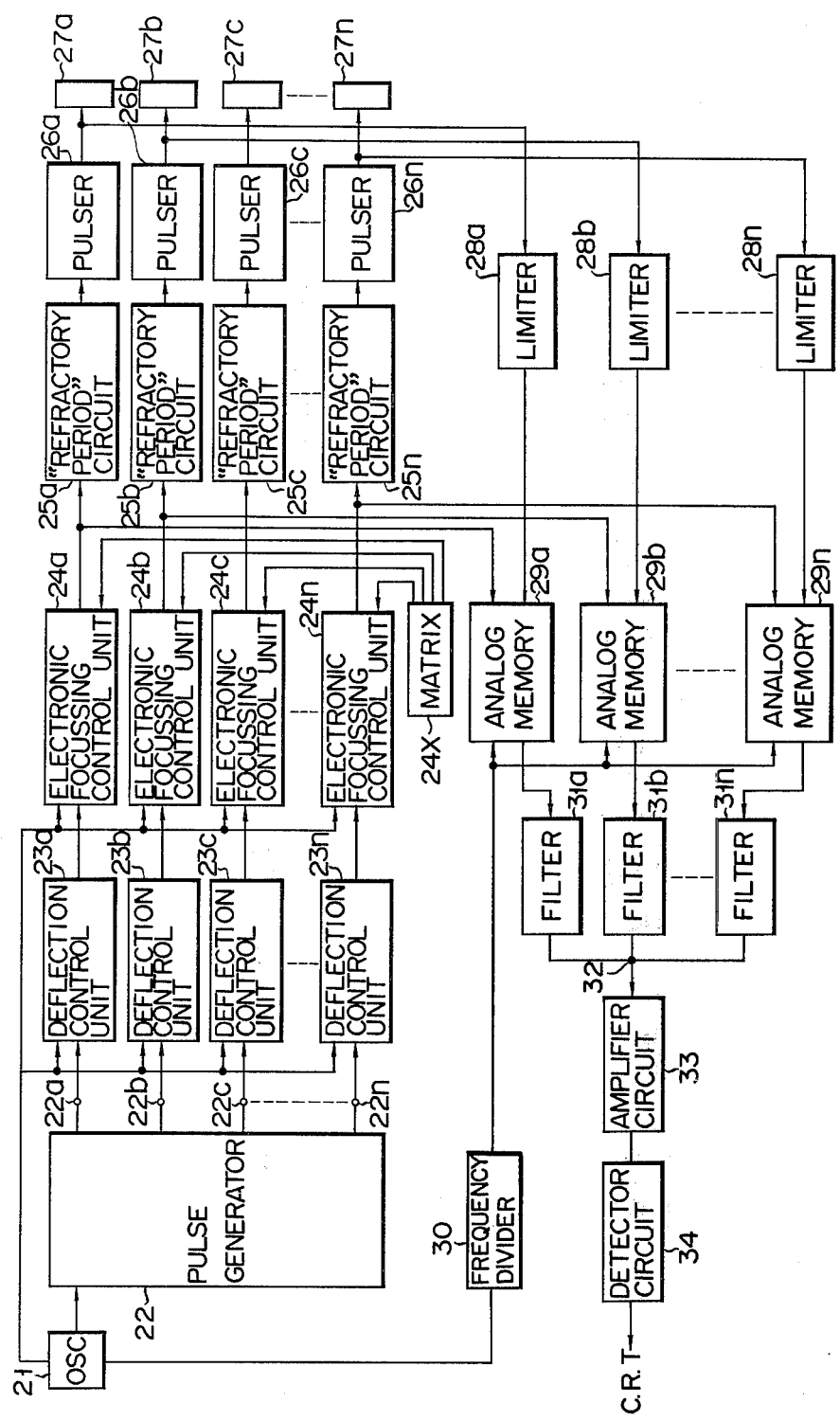
FIG. 1 is a block diagram of an ultrasonic wave transmitting and receiving apparatus according to the embodiment of this invention.

One embodiment of this invention will now be described by referring to the accompanying drawings.

An oscillator 21 for generating a pulse signal of a predetermined frequency, for example, $fo = 40$ MHz is coupled to a control pulse generator 22. The control pulse generator 22 sequentially generates control pulses, in a cyclically varied delay time relation, from its output terminals 22a to 22n in response to the output pulse of the oscillator as will be described later. The output terminals 22a ... 22n of the control pulse generator are also connected to deflection control units 23a ... 23n, respectively, adapted to control the deflection of ultrasonic wave beams. The output terminals of the deflection control units 23a ... 23n are connected to electronic focussing control units 24a ... 24n, respectively, adapted to control the focussing of the ultrasonic beams. The electron focussing control units 24a ... 24n digitally control the output pulses of the deflection control units 23a ... 23n in a predetermined delay time relationship. The delay times of the electron focussing control units are determined by preset signals of a matrix circuit 24x, respectively. The output terminals of the electron focussing control units 24a . . . 24n are connected respectively through "refractory period" circuits 25a . . . 25n to pulses 26a . . . 26n, the outputs of which are coupled to electro-acoustic conversion elements 27a . . . 27n, respectively. The above-mentioned circuit arrangement constitutes a transmission section of an ultrasonic transmitting and receiving apparatus.

In the wave reception section of the ultrasonic transmitting and receiving apparatus, the electroacoustic conversion elements 27a . . . 27n are connected respectively through limiters 28a . . . 28n to analog memories 29a . . . 29n. The analog memories 29a . . . 29n, each, effect a write-in operation by a pulse signal obtained by frequency-dividing output pulses of the oscillator 21 into a predetermined frequency through a frequency divider 30, and effect a readout operation by output pulses of the electronic focussing control units 24a . . . 24n. Readout signals of the analog memories 29a . . . 29n are added together at a junction 32 through filters 31a . . . 31n, respectively. The synthesized signal is coupled through an amplifier circuit 33 and detector circuit 34 to a cathode ray tube CRT 35 where it is converted into a visual image.

The operation of the above-mentioned ultrasonic transmitting and receiving apparatus will now be explained below.

Figure 2:
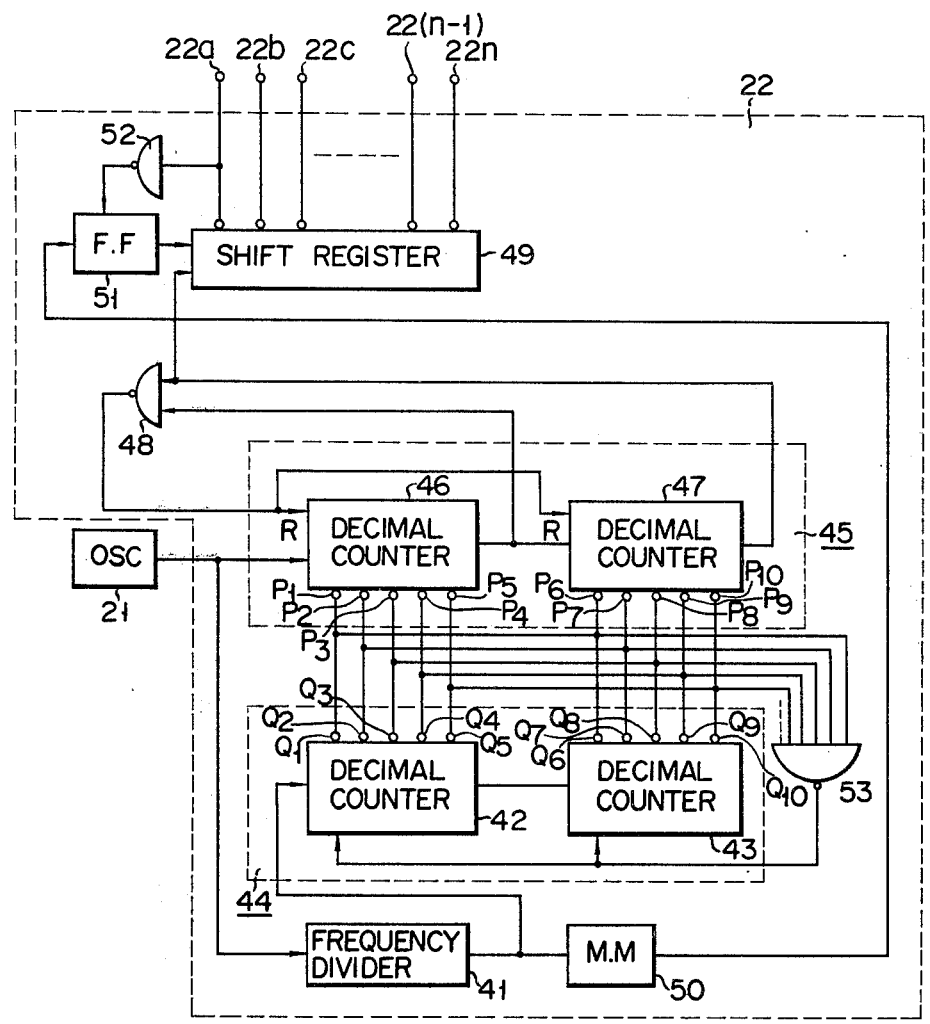
FIG. 2 is a detailed circuit arrangement of one of control pulse generators in the apparatus shown in FIG. 1.
Figure 3:
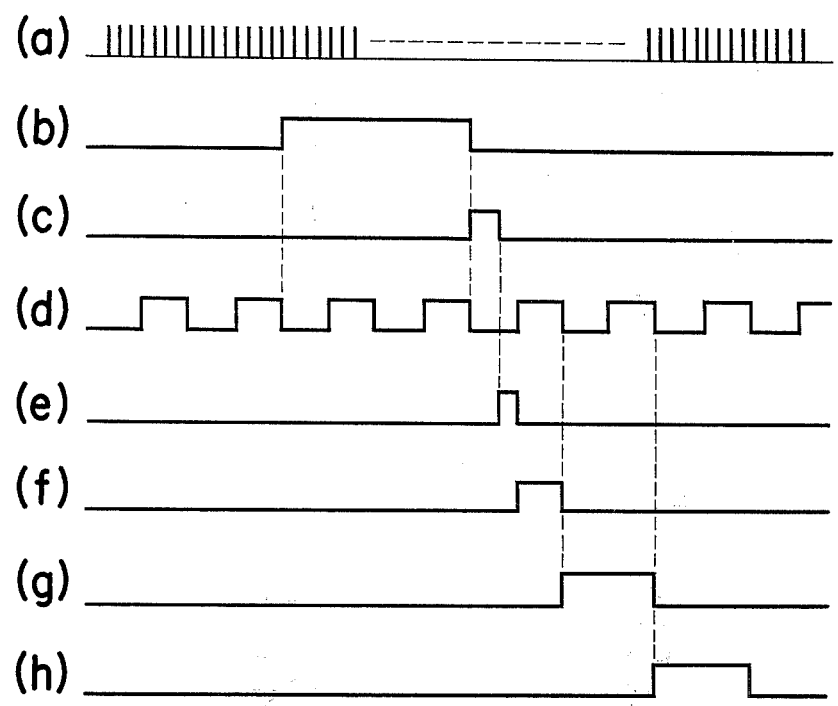
FIG. 3 shows time chart corresponding to each part of the circuit of FIG. 2.

FIG. 2 is a circuit arrangement of the control pulse generator 22. The pulse signal of, for example, 40 MHz as shown in FIG. 3(a) which is generated from the oscillator 21 is frequency-divided by a frequency divider 41 into a pulse signal of, for example, 4 KHz as shown in FIG. 3(b). The output pulse signal of the frequency divider 41 is coupled to a counter circuit 44 comprising two decimal counters 42 and 43. The counter circuit 44 is preset by an output pulse of the frequency divider 41. Output terminals $Q_1$ to $Q_5$ and $Q_6$ to $Q_{10}$ of the decimal counters 42 and 43, respectively, in the counter circuit 44 are coupled to input terminals $P_1$ to $P_5$ and $P_6$ to $P_{10}$ of decimal counters 46 and 47, respectively, in a counter circuit 45. The counter circuit 45 is preset by output signals of the output terminals of the decimal counters 42 and 43, respectively, in the counter circuit 44. The output terminals of the decimal counters 46 and 47 in the counter circuit 45 are connected through a NAND gate 48 to a reset terminal R of each of the decimal counters 46 and 47 in the counter circuit 45, and when the outputs of the decimal counters 46 and 47 are both "1"s, the decimal counters 46 and 47 are reset. The output frequency of the oscillator 21 is divided, according to the preset value of the counter circuit 45, into a pulse signal as shown in FIG. 3(d) and the output of the counter circuit 45 is supplied to the shift register 49. An ouput pulse (b) of the frequency divider 41 is delivered to a one-shot multivibrator 50. The output pulse of the one-shot multivibrator 50 as shown in FIG. 3(c) is supplied to a flip-flop circuit FF51 which in turn supplies a pulse signal as shown in FIG. 3(e) to the shift register 49. The content of the shift register 49 is shifted under control of the clock pulse of the counter circuit 45 as shown in FIG. 3(d), and the shift register 49 sequentially generates mutually delayed output pulses from its output terminals 22a . . . 22n, though only the output pulses (f) . . . (h) of the output terminals 22a . . . 22c are shown in FIG. 3. When the output pulse corresponding to the output terminal 22a of the shift register 49 appears, it is coupled through a NAND gate 52 to the flip-flop circuit FF51 to cause the latter to be reset. The counter circuit 44 causes its state to be varied an amount corresponding to "1" by the output pulse of the frequency divider 41 and the counter 45 is preset into a new preset value by a preset signal from each of the output terminals $Q_1$ to $Q_5$ and $Q_6$ to $Q_{10}$ of the decimal counters 42 and 43 in the counter circuit 44. The output pulse of the one-shot multivibrator 50 triggers the flip-flop 51. The pulse signal supplied to the counter circuit 45 from the oscillator 21 is divided into a pulse signal according to the preset value of the counter circuit 45 and the content of the shift register 49 is shifted by the output of the counter circuit 45. As a result, with a delay time corresponding to the frequency of clock pulses of the shift register 49, pulse signals are sequentially generated from the output terminals 22a . . . 22n of the shift register 49. In this way, with the cyclically varied delay time relation, the pulse signals sequentially appear from the output terminals 22a . . . 22n of the shift register 49.

The setting of the delay time will now be explained in more detail.

Suppose that the frequency of the output pulse signal of the oscillator 21 is divided by the counter 45 into a 1/N pulse signal (wherein N is an integer). In this case, the nines complement of N is preset as a binary format into the counters 46 and 47 in the counter circuit 45 by the preset signals of the counters 42 and 43, provided that, at $N > 9$, $N_1$ and $N_2$ having a relation of $$N = 10N_1 + N_2$$
$$N_1 N_2 \leq 9$$

are preset into the counters 46 and 47, respectively, in the counter circuit 45. With respect to $N_1$, $9-N_1$ is preset into the counter 46 and with respect to $N_2$, $9-N_2$ into the counter 47. In this case, the shifting operation of the shift register 49 is effected at a time interval of $N/fo$. The time interval means a delay time between the output pulses generated from the shift register 49. Such sequentially varied signals as $9-(N_2-1)$, $9-(N_2-2)$, . . . are generated, in response to the output pulses of the frequency divider 41, from the output terminals $Q_1$ to $Q_5$ and $Q_6$ to $Q_{10}$ of the decimal counters 42 and 43 in the counter circuit 44, and the counters 46 and 47 in the counter circuit 45 are preset into the above-mentioned states i.e. the frequency-division rate. Each time the counter circuit 45 is preset by the output of the counter circuit 44, the frequency division ratio of the counter circuit 45 with respect to the output pulse of the oscillator is sequentially increased, and the frequency of clock pulses supplied to the shift register 49 is raised in such a state of $fo/N-1$, $fo/N-2$ . . . A delay time between pulse signals sequentially generated from the shift register 49 is gradually shortened in such a state as $N-1/fo$, $N-2/fo$ . . . That is, by so doing the delay time is sequentially varied at an integral multiple of $1fo$. As a consequence, ultrasonic waves generated from the electro-acoustic conversion elements, which are driven by the pulse signals with such a delay time, have their directionality consecutively varied with variation in the delay time.

As the counter circuit 45 comprises the serially connected two decimal counters 46 and 47 as shown in FIG. 2, the delay time can be sequentially varied up to one hundredfold of $1/fo$ at maximum. If the output pulses of the output terminals $Q_1$ to $Q_5$ and $Q_6$ to $Q_{10}$ of the counters 42 and 43 in the counter circuit 44 are fed back to the counters 42 and 43 through a NAND gate 53, with the time corresponding to a given integral multiple of 1/fo being considered as an upper limit of the delay time, the delay time can be sequentially varied in a range up to the above-mentioned upper limit.

Since an output pulse on the output terminal 22n is always delayed with respect to an output pulse on the output terminal 22a of the pulse generator 22, if the electro-acoustic conversion elements 27a ... 27n are directly driven by the output pulses of the output terminals 22a ... 22n of the pulse generator 22, the beams of ultrasonic waves from the electro-acoustic conversion elements are deflected in either right or a left direction with a zero degree as a center. One solution to this problem is to permit the content of the shift register 49 to be shifted in both the right and left directions. This problem is also eliminated by coupling the deflection control units 23a ... 23n to the output terminals of the pulse generator 21 as shown in FIG. 1. The deflection control units 23a ... 23n are so constructed as to simultaneously generate output signals when the counters 46 and 47 in the counter circuit 45 are preset, for example, into N/2. This makes it possible to deflect the beams of ultrasonic waves in both the right and left directions. Stated in another way, the deflection direction of the beam of ultrasonic waves can be varied by displacing its zero-degree point.

Figure 4:
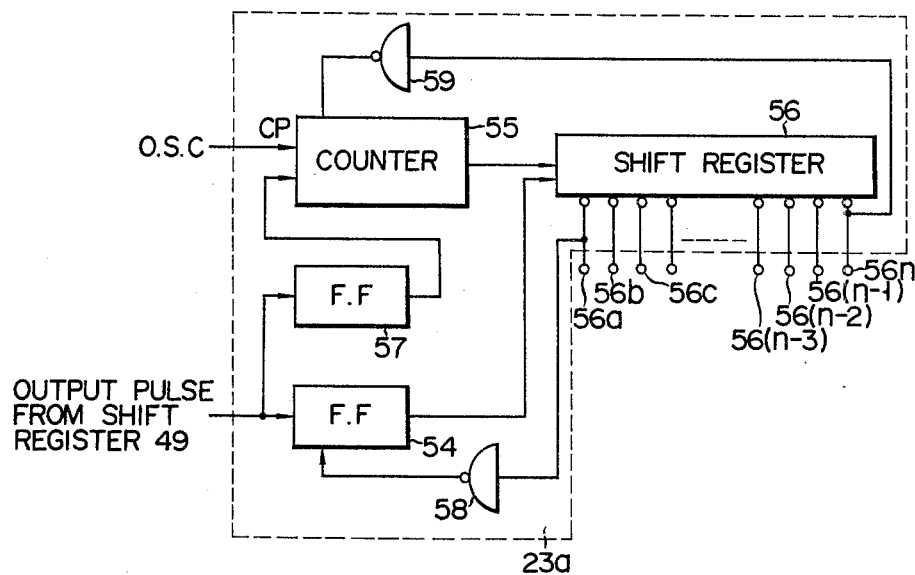
FIG. 4 is a detailed circuit arrangement of one of deflection control units in the apparatus shown in FIG. 1.

FIG. 4 shows one (i.e. unit 23a) of the deflection control units 23a ... 23n in FIG. 1. The deflection control unit 23a includes flip-flop circuits 54 and 57 to which is coupled a pulse signal from the output terminal 22a of the shift register 49 in the pulse generator 22. The output of the flip-flop 54 is coupled to one input terminal of a shift register 56 and the output of the flip-flop 57 is coupled to a set terminal of counter 55. The counter 55 is coupled to the pulse oscillator 21 so as to receive the pulse signal from the latter. The output of the counter 55 is coupled to the other input terminal of the shift register to permit the content of the shift register 56 to be shifted. If the counter circuit 45 in the pulse generator 22 is preset into N0/2, since an output signal on the output terminal 22n of the shift register 49 is delayed a time of (N−1)No/2fo with respect to an output signal on the output terminal 22a of the shift register 49 in the pulse generator 22, it is required that in order for the corresponding deflection control units 23a and 23n to simultaneously generate output signals in response to the pulse signals from the terminals 22a and 22n of the shift register 49 the deflection control unit 23a generate a signal with a time delay of (N−1)No/2fo. If the deflection control units 23b, 23c ... 23n−1 corresponding to the output terminals 22b, 22c ... 22n−1 are designed to generate output pulses, with the corresponding delay times (N−2)No/2fo, (N−3)No/2fo ... (N−n−1)No/2fo, in response to the corresponding output pulses from the shift register 49, all the deflection control units 23a ... 23n can simultaneously generate output pulses.

The above-mentioned operation will be explained in connection with the circuit of FIG. 4.

The counter 55 comprising a scale-of-No/2 counter is adapted to count the output pulses from the oscillator 21 in response to the output pulses of the flip-flop circuit 57 operated in response to pulse signals from the output terminals 22a of the shift register 49 in the pulse generator 22. Output pulses generated for each N/2 count cycle from the counter 55 are supplied as clock pulses to the shift register 56 and the content of the shift register 56 is shifted in response to the clock pulses of the counter 55 in the deflection control unit 23a to sequentially generate output pulses each with a time delay of No/2fo from output terminals 56a ... 56n of the shift register 56 in the deflection control unit 23a. An output pulse on the output terminal 56a of the shift register 56 is delayed a time of (N−1)No/2fo with respect to an output pulse on the output terminal 56n of the shift register 56. If, therefore, an output pulse is extracted from the output terminal 56n of the shift register 56 in the deflection control unit 23a and from the output terminal 56a of the shift register 56 in the deflection control unit 23n, output pulses can be time-coincidentally obtained from the deflection control units 23a and 23n. That is, for the preset value of No12 output pulses can be time-coincidentally obtained from the deflection control units 23a ... 23n by suitably selecting the output terminals 56a ... 56n of the deflection control units 23a ... 23n.

When the counter circuit 45 in the pulse generator 22 is preset into No12 + 1, output pulses are sequentially generated with a time delay of (No12 + 1)/fo from the output terminals 22a ... 22n of the shift register 49 in the pulse generator 22. Since the counters 55 of the deflection control units 23a ... 23n are also preset into No/2 + 1, they have a delay time of No/2fo with respect to each other. Where, therefore, the deflection control units 23a ... 23n are driven by output pulses generated based on the new preset value from the pulse generator 22, the deflection control unit 23n generates an output pulse with a delay time of $$\frac{(N-1)}{f_o}\left(\frac{N_o}{2}+1\right)-\left(\frac{(N-1)N_o}{2f_o}\right)=\frac{N-1}{f_o}$$

with respect to the output pulse of the deflection control unit 23a. That is, pulse signals are sequentially generated with a time delay of 1/fo from the deflection control units 23a ... 23n. When the counter circuit 45 is preset into No/2 + 2, output pulses are sequentially generated with a time delay of 2/fo from the deflection control units 23a ... 23n.

When these output pulses are supplied to the electro-acoustic conversion elements, the beams of ultrasonic waves are deflected in both the right and left directions with a zero degree as a center. The flip-flop circuits 54 and 55 are reset by pulses passed respectively through NAND gates 58 and 59 in the deflection control unit.

In order to bring the beams of ultrasonic waves, output pulses of the deflection control units 23a ... 23n are delivered to the electron focussing units 24a ... 24n, respectively.

Figure 5:
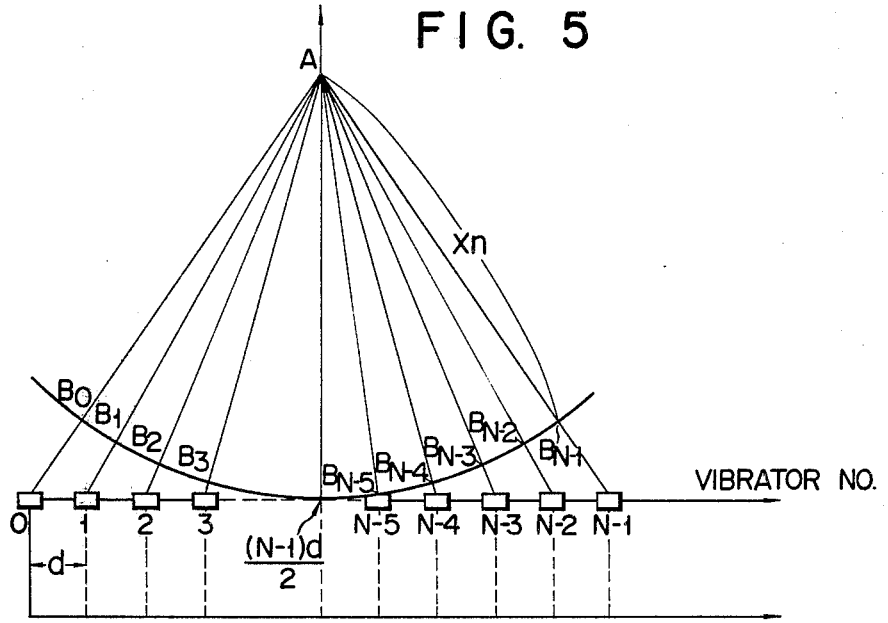
FIG. 5 is an explanatory view for explaining a principle of electronic focussing.

The electron focussing units 24a ... 24n are so constructed as to meet the requirement as shown in FIG. 5. In the Figure, N electro-acoustic conversion elements, numbered "0" to "N−1" are arranged in line at intervals of d on a plane, a focussing point A is determined on an axis drawn vertically from a center position (N−1)d/2 of the in-line arrangement of the electroacoustic conversion elements, and an arc with a radius Xn is drawn through the center position (N−1)d/2 of the in-line arrangement with the focussing point A as a center. The intersections of the arc and lines drawn from the focus A to the electroacoustic conversion elements 0, 1, ... N−2 and N−1 being represented by $B_0, B_1 ... B_{n-2}$ and $B_{n-1}$, respectively. The beam of ultrasonic wave radiates toward the focussing point A from the 0-th electro-acoustic conversion element arrives at the focussing point A with a time delay of $$B_0 0 = \{ \sqrt{X^2 n + (N-1)^2 d^2/4} - Xn \ /C \ \}$$

with respect to the beam of ultrasonic wave radiates toward the focussing point A from the center position, i.e. the central electro-acoustic conversion element, of the in-line arrangement. If, therefore, the 0-th electroacoustic conversion element at the edge of the in-line arrangement is driven earlier than the central electroacoustic conversion element of the in-line arrangement by an amount corresponding to the above-mentioned time delay, the beams of ultrasonic waves from both the 0-th and central electro-acoustic conversion elements of the in-line arrangement arrive at the focussing point A in an in-phase relationship. If the other electroacoustic conversion elements 2, 3 . . . N−2 are also driven earlier than the central electroacoustic conversion element of the in-line arrangement by amounts corresponding to times $B_1 1, B_2 2 \ldots B(N-1) \cdot N-1$, then the beams of ultrasonic waves from the electro-acoustic conversion elements 0 to N−1 are focussed at the focussing point A.

Figure 6:
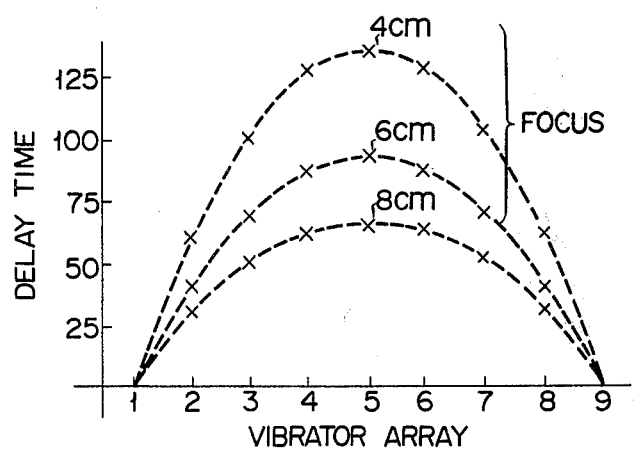
FIG. 6 is a view for explaining a relation between a focussing point of the beams of ultrasonic waves and a delay time.

The so constructed electronic focussing control units $24a \ldots 24n$, each, constitute a counter adapted to count pulses from the oscillator 21 in response to the output of the corresponding deflection control unit, and the counter is preset by the preset signal of the matrix circuit 24x to generate an output in the above-mentioned time relationship. Suppose, for example, that a scale-of-5 counter is used as the electronic focussing control unit. Then, the scale-of-5 counters generate an output pulse of a frequency $fo/5$, with a deflection delay time corresponding to an integral multiple of $1/fo$, in response to the output pulse of the corresponding deflection control unit. By using the scale-of-5 counter a focussing delay time of $5 \times 25 = 125$ nsec at maximum can be controlled at the matrix circuit 24x. This means that as shown in FIG. 6 the beam of ultrasonic wave can be focussed at a distance of 4 cm. It is to be noted that FIG. 6 shows a plot of a delay time against each focussing point of 4, 6 and 8 cm. The delay times obtained from the respective electronic focussing control counters $24a \ldots 24n$ show approximate values to the values of FIG. 6 and, however, this presents no problem from the practical viewpoint.

The rectangular wave output pulses of the electronic focussing control units $24a \ldots 24n$ are delivered to the "refractory period" circuits $25a \ldots 25n$ where only a first rise portion of the rectangular wave output pulse is extracted. The output pulses of the "refractory period" circuits $25a \ldots 25n$ are supplied to the pulsers $26a \ldots 26n$ and the pulsers $26a \ldots 26n$ generate high voltage impulses (about 500V) for supplying to the electroacoustic conversion elements $27a \ldots 27n$. By so doing the focussed beams of ultrasonic waves are radiated for an object.

When the beams of ultrasonic waves are reflected from a desired portion within the living body, the reflected beam is received by the electro-acoustic conversion elements $27a \ldots 27n$ for conversion to corresponding electrical signals. The signals of the electroacoustic conversion elements $27a \ldots 27n$ are supplied as receiving signals to the analog memories $29a \ldots 29n$ respectively through the limiters $28a \ldots 28n$ adapted to limit the initial pulse.

Figure 7:
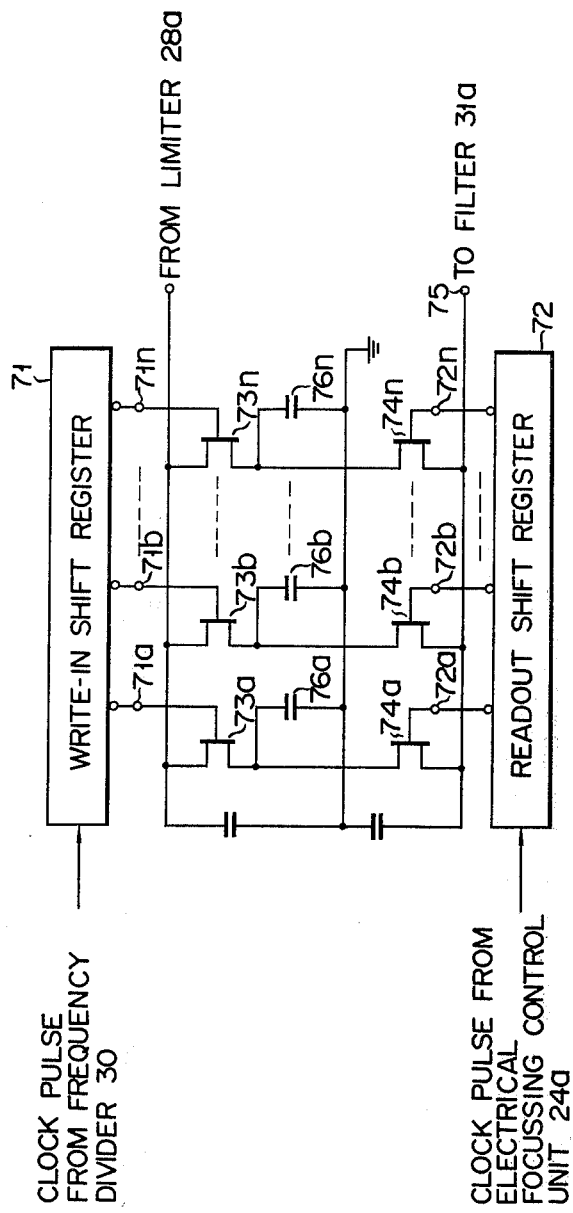
FIG. 7 is a circuit arrangement of one of analog memories shown in the apparatus in FIG. 1.

The analog memories $29a \ldots 29n$, each, include a write-in shift register 71 and readout shift register 72 as shown in FIG. 7. The write-in shift register 71 in the analog memory is adapted to receive an 8 MHz clock pulse into which the 40 MHz output of the oscillator 21 is frequencydivided by the frequency divider 30. For example, the readout shift register 72 of the analog memory 29a is adapted to receive an output pulse of the electron focussing control unit 24a as a clock pulse. Between a terminal 71a of the write-in shift register 71 and a terminal 72a of the readout shift register 72 are connected a first field effect transistor FET) 73a which has a gate coupled to the terminal 71a of the write-in shift register 71, a drain adapted to receive a signal from the limiter 28a and a source grounded through a capacitor 76a, and a second FET 74a which has a gate coupled to the terminal 72a, a drain coupled to the source of the first FET 73a and a source coupled to an output terminal 75; . . . ; and between a terminal 71n of the write-in shift register 71 and a terminal 72n of the readout shift register 72 are connected a first FET 73n which has a gate coupled to the terminal 71n of the write-in shift register 71, a drain adapted to receive the signal from the limiter 28a and a source grounded through a capacitor 76n, and a second FET 74n which has a gate coupled to the terminal 72n, a drain coupled to the source of the first FET 73n and a source coupled to the output terminal 75.

When a clock pulse the frequency of which is the same as an output pulse of the electron focussing control unit 24a is supplied through the frequency divider 30 to the write-in shift register 71, an output pulse is generated from the output terminal 71a of the write-in shift register 71 to cause conduction between the source and drain of the FET 73a, permitting the reception signal from the limiter 28a to be stored in the capacitor 76a. In this way, output pulses are sequentially generated from the output terminals $71b \ldots 71n$ of the write-in shift register 71 in receipt of the clock pulses passed through the frequency divider 30 from the oscillator 21 to cause te FET's $73b \ldots 73n$ to be sequentially turned ON. As a result, the receiving signals corresponding to echo levels from the electroacoustic conversion element 27a are sequentially stored into the capacitors 76b to 76n.

Those electric charges so stored in the capacitors $76b \ldots 76n$ which correspond to the receiving signals passed through the limiter 28a from the electro-acoustic conversion element 27a are read out from the output terminal 75 through sequential conduction of the second FET's $74a \ldots 74n$ by output pulses of the readout shift register 72, with the same delay time as that of the electron focussing control unit 24a, by the output pulse of the electron focussing control unit 24a.

The other analog memories $29b \ldots 29n$ are likewise adapted to receive the corresponding receiving signals at the timing of the clock pulse from the frequency divider 30 and read out the corresponding write-in electric charges at the timing of the output pulses of the corresponding electronic focussing control units $24b \ldots 24n$. That is, the receiving signals generated with a different delay time from the electro-acoustic conversion elements $27a \ldots 27n$ are stored in the corresponding analog memories $29a \ldots 29n$, and the stored signals of the analog memories $29a \ldots 29n$ are read out in response to output pulses generated with a different delay time from the electron focussing control units $24a \ldots 24n$. The readout outputs of the analog memories 29a ... 29n are coupled respectively through the filters 31a ... 31n to the junction 32 where they are added together. The combined output signals are fed through the amplifier circuit 33 and detector circuit 34 to the cathode ray tube (CRT).

According to this invention the receiving signals are written, in the form of electric charges corresponding to the above-mentioned echo levels, into the analog memories at the timing of the reference signal at reception, and the electric charges of the analog memories are read out with the predetermined time delays. Since the receiving signals are digitally treated in this way, an accurate phase control can be effected without using any L.C. delay lines and it is also possible to broaden the frequency band. Furthermore, as the delay time of the reception wave can be varied merely by varying the delay time for the transmission signal, the transmitting and receiving apparatus can be made compact as a whole.

What is claimed is:

1. An ultrasonic transmitting and receiving apparatus comprising
    a plurality of electro-acoustic conversion elements arranged in line;
    a plurality of driving pulsers for supplying high voltage driving pulses to the electro-acoustic conversion elements to permit them to generate ultrasonic beams;
    a plurality of electronic focussing control units for energizing the driving pulsers in a predetermined time relation in order to focus the ultrasonic beams;
    a clock pulse generator for generating fundamental clock pulses;
    a control pulse generator having a plurality of output terminals for sequentially generating control output pulses through the output terminals with equal delay times which are cyclically varied in a digital format;
    a plurality of deflection control units for deflecting the ultrasonic beams which are generated to correspond with the output terminals of the control pulse generator to generate output pulses in response to the control pulses from the control pulse generator which have a delay function in order to simultaneously generate output pulses in response to the control output pulses seqentially generated from the control pulse generator with a desired delay time which may be cyclically varied in order to determine a deflection center, the output pulses from the deflection control units being supplied to the electronic focussing control units, respectively; and
    a plurality of memory units corresponding to the electro-acoustic conversion elements adapted to receive, as write-in signals, signals obtained from the electro-acoustic conversion elements when the ultrasonic beams are reflected from an object and to read out the write-in signals at the same intervals as the output pulses generated by the electronic focussing control units.

2. An ultrasonic transmitting and receiving apparatus according to claim 1 wherein the control pulse generator comprises a counter circuit having a preset value which is cyclically varied for sequentially generating output pulses with a time delay corresponding to the preset value and a shift register having a plurality of output terminals for sequentially generating control pulses through the output terminals in response to the output pulses from the counter circuit.

3. An ultrasonic transmitting and receiving apparatus according to claim 1 in which the control pulse generator comprises
    a frequency divider for frequency dividing fundamental clock pulses supplied to the control pulse generator into clock pulses having a predetermined value;
    a first counter circuit driven by output pulses of the frequency divider;
    a second counter circuit preset by output signals of the first counter circuit for frequency dividing the clock pulses in accordance with the predetermined values; and
    a shift register for sequentially generating output pulses, with a delay time determined by the frequency of the frequency divided clock pulses from the second counter circuit, from a plurality of output terminals in response to the frequency divided clock pulses of the second counter circuit.

4. An ultrasonic transmitting and receiving apparatus according to claim 3, in which said first counter comprises a preceding stage counter driven by said further clock pulse and a succeeding stage counter driven by an output pulse of said preceding stage counter, said counters having a plurality of output terminals from which the output signals are applied as presetting signals to said second counter circuit.

5. An ultrasonic transmitting and receiving apparatus according to claim 1, in which said second counter circuit comprises a preceding stage counter preset by first presetting signals of said first counter circuit and a succeeding stage counter driven by an output pulse of said preceding stage counter and preset by second presetting signals of said first counter circuit; and an output pulse of said succeeding stage counter is applied as a clock pulse to said shift register.

6. An ultrasonic transmitting and receiving apparatus according to claim 4, in which preset output signals of said preceding and succeeding stage counters in said first counter circuit are fed back to said counters through a NAND gate circuit.

7. An ultrasonic transmitting and receiving apparatus according to claim 1, in which said deflection control units, each, comprise a counter adapted to be triggered by control pulses from the corresponding output terminal of said control pulse generator, count said clock pulse and generate output pulses according to preset values of said counter; and a shift register adapted to receive output pulses as clock pulses from said counter to sequentially generate output pulses from a plurality of output terminals with a time delay corresponding to the preset values of said counter; and a predetermined one of said output terminals of said shift register is coupled to the corresponding electronic focussing unit.

8. An ultrasonic transmitting and receiving apparatus according to claim 1, in which said electronic focussing control units, each, comprise a counter for counting the fundamental clock pulses supplied thereto in response to output pulses of the corresponding deflection control unit and generate and output pulse in response to a variable preset value; those axisymmetric ones of said electro-acoustic conversion elements are preset to the same preset values which become gradually smaller when they are viewed from the electro-acoustic conversion element at or near the center of an array of the electro-acoustic conversion elements toward each edge of the axisymmetric array.

9. An ultrasonic transmitting and receiving apparatus according to claim 8, in which said electronic focussing control device includes a matrix circuit for supplying preset signals to the electron focussing control unit counters.

10. An ultrasonic transmitting and receiving apparatus according to claim 1, in which said memory units, each, comprise a write-in shift register for sequentially generating write-in pulses from a plurality of output terminals in response to clock pulses of a predetermined frequency; first semiconductor switches adapted to be sequentially operated by the write-in pulses of said write-in shift register; memory elements adapted to sequentially store the reflection wave signals by operation of said semiconductor switches; a readout shift register for sequentially generating readout output pulses from its output terminals in response to an output pulse of the corresponding electron focussing control unit; second semiconductor switches operated in response to the readout output pulses of the readout shift register to sequentially read out the contents of the memory elements.

* * * * *